(12) United States Patent
Belson et al.

(10) Patent No.: US 9,277,915 B2
(45) Date of Patent: Mar. 8, 2016

(54) METHOD AND APPARATUS FOR TRANSAPICAL ACCESS AND CLOSURE

(75) Inventors: Amir Belson, Los Altos, CA (US);
Phillip Charles Burke, Pala, CA (US);
Eric Thomas Johnson, Temecula, CA (US); Bauback Safa, San Francisco, CA (US)

(73) Assignee: VasoStitch, Inc., Los Altos, CA (US)

( * ) Notice: Subject to any disclaimer, the term of this patent is extended or adjusted under 35 U.S.C. 154(b) by 120 days.

(21) Appl. No.: 13/169,454

(22) Filed: Jun. 27, 2011

(65) Prior Publication Data

US 2012/0116418 A1    May 10, 2012

Related U.S. Application Data

(60) Provisional application No. 61/398,485, filed on Jun. 26, 2010, provisional application No. 61/402,042, filed on Aug. 23, 2010.

(51) Int. Cl.
*A61B 17/04* (2006.01)
*A61B 17/06* (2006.01)
(Continued)

(52) U.S. Cl.
CPC ............. *A61B 17/0469* (2013.01); *A61B 17/06* (2013.01); *A61B 17/3403* (2013.01); *A61B 17/3421* (2013.01); *A61B 2017/00243* (2013.01); *A61B 2017/00247* (2013.01); *A61B 2017/00575* (2013.01); *A61B 2017/00663* (2013.01); *A61B 2017/0243* (2013.01); *A61B 2017/0417* (2013.01); *A61B 2017/0472* (2013.01);
(Continued)

(58) Field of Classification Search
CPC .......... A61B 17/0482; A61B 17/0469; A61B 17/06; A61B 2017/06052; A61B 2017/06076; A61B 2017/061; A61B 2017/00247; A61B 2017/00663

USPC .................................. 606/139, 144, 148, 228
See application file for complete search history.

(56) References Cited

U.S. PATENT DOCUMENTS 4,204,541 A    5/1980   Kapitanov
4,641,652 A    2/1987   Hutterer et al.
(Continued)

FOREIGN PATENT DOCUMENTS

CN          1886096 A      12/2006
WO     WO 98/52473 A1     11/1998
(Continued)

OTHER PUBLICATIONS

European search report and opinion dated Jun. 14, 2013 for EP Application No. 10753932.2.
(Continued)

*Primary Examiner* — Todd J Scherbel
(74) *Attorney, Agent, or Firm* — Wilson Sonsini Goodrich & Rosati

(57) ABSTRACT

Methods and apparatus for providing transapical access to a heart chamber for performing an intra cardiac procedure are described. The apparatus include a helical needle driver, a dilator, a straight access needle, and optionally a guidewire. After entering the heart chamber with the straight access needle, the helical needle driver is used to place a helical suture within the myocardium. After removing the needle driver, the dilator is advanced through the pre-placed helical suture, dilating both a passage and the circumscribing suture. After performing procedure, the pre-placed suture may be closed by proximally retracting an external end of the suture.

26 Claims, 11 Drawing Sheets

(51) Int. Cl.
*A61B 17/34* (2006.01)
*A61B 17/00* (2006.01)
*A61B 17/02* (2006.01)
*A61B 18/00* (2006.01)

(52) U.S. Cl.
CPC ............... *A61B2017/06042* (2013.01); *A61B 2017/06052* (2013.01); *A61B 2017/06076* (2013.01); *A61B 2017/06176* (2013.01); *A61B 2017/3405* (2013.01); *A61B 2017/3427* (2013.01); *A61B 2017/3458* (2013.01); *A61B 2017/3488* (2013.01); *A61B 2018/00392* (2013.01)

(56) References Cited

U.S. PATENT DOCUMENTS

| | | | |
|---|---|---|---|
| 4,964,468 A | | 10/1990 | Adams et al. |
| 5,356,424 A * | | 10/1994 | Buzerak et al. ............... 606/223 |
| 5,407,527 A | | 4/1995 | Ferrante et al. |
| 5,527,342 A | | 6/1996 | Pietrzak et al. |
| 5,545,148 A | | 8/1996 | Wurster |
| 5,562,685 A | | 10/1996 | Mollenauer et al. |
| 5,577,993 A * | | 11/1996 | Zhu et al. .................. 600/204 |
| 5,626,613 A | | 5/1997 | Schmieding |
| 5,782,844 A | | 7/1998 | Yoon et al. |
| 5,820,631 A | | 10/1998 | Nobles |
| 5,931,855 A | | 8/1999 | Buncke |
| 5,947,983 A | | 9/1999 | Solar et al. |
| 6,287,250 B1 * | | 9/2001 | Peng et al. .................. 600/37 |
| 6,626,917 B1 * | | 9/2003 | Craig .......................... 606/144 |
| 7,637,918 B2 | | 12/2009 | Dant |
| 7,758,595 B2 | | 7/2010 | Allen et al. |
| 7,780,701 B1 | | 8/2010 | Meridew et al. |
| 8,500,757 B2 * | | 8/2013 | Miraki et al. ................. 606/144 |
| 2003/0074023 A1 | | 4/2003 | Kaplan et al. |
| 2004/0002735 A1 | | 1/2004 | Lizardi et al. |
| 2004/0060410 A1 | | 4/2004 | Leung et al. |
| 2004/0138706 A1 | | 7/2004 | Abrams et al. |
| 2004/0147957 A1 | | 7/2004 | Pierson, III |
| 2005/0021057 A1 | | 1/2005 | St. Goar et al. |
| 2005/0070959 A1 | | 3/2005 | Cichocki, Jr. |
| 2005/0165414 A1 | | 7/2005 | Craig |
| 2005/0267520 A1 | | 12/2005 | Modesitt |
| 2006/0036265 A1 | | 2/2006 | Dant |
| 2006/0074484 A1 * | | 4/2006 | Huber .......................... 623/2.11 |
| 2006/0212048 A1 | | 9/2006 | Crainich |
| 2006/0253127 A1 | | 11/2006 | Bjerken |
| 2007/0005109 A1 | | 1/2007 | Popadiuk et al. |
| 2007/0027454 A1 | | 2/2007 | Modesitt |
| 2007/0112422 A1 * | | 5/2007 | Dehdashtian ................. 623/2.11 |
| 2008/0109036 A1 * | | 5/2008 | Stopek et al. ................. 606/232 |
| 2008/0234731 A1 | | 9/2008 | Leung et al. |
| 2008/0275473 A1 | | 11/2008 | Filipi et al. |
| 2008/0306333 A1 * | | 12/2008 | Chin ........................... 600/104 |
| 2009/0054926 A1 | | 2/2009 | Pipenhagen et al. |
| 2009/0082788 A1 * | | 3/2009 | ElMaraghy ................ 606/148 |
| 2009/0187116 A1 | | 7/2009 | Noishiki et al. |
| 2009/0240264 A1 * | | 9/2009 | Tuval et al. ................ 606/148 |
| 2009/0275960 A1 | | 11/2009 | Provenza et al. |
| 2009/0287183 A1 | | 11/2009 | Bishop et al. |
| 2010/0063542 A1 | | 3/2010 | Van Der Burg et al. |
| 2010/0087855 A1 | | 4/2010 | Leung et al. |
| 2010/0114306 A1 * | | 5/2010 | Lenihan et al. ............. 623/2.11 |
| 2010/0268253 A1 | | 10/2010 | Ahlberg et al. |
| 2010/0274129 A1 | | 10/2010 | Hooven |
| 2011/0004235 A1 | | 1/2011 | Sundt, III et al. |
| 2011/0015728 A1 | | 1/2011 | Jimenez et al. |
| 2011/0190811 A1 * | | 8/2011 | Shanley ...................... 606/213 |
| 2011/0238090 A1 * | | 9/2011 | Heneveld ..................... 606/144 |
| 2012/0035654 A1 | | 2/2012 | Belson |
| 2012/0065677 A1 | | 3/2012 | West |
| 2012/0089181 A1 | | 4/2012 | Shanley et al. |
| 2012/0143226 A1 | | 6/2012 | Belson et al. |
| 2015/0073478 A1 | | 3/2015 | Belson et al. |
| 2015/0265272 A1 | | 9/2015 | Belson et al. |

FOREIGN PATENT DOCUMENTS

| | | |
|---|---|---|
| WO | WO 2007/098212 A2 | 8/2007 |
| WO | WO 2007/098212 A3 | 7/2008 |
| WO | WO 2009/021161 A1 | 2/2009 |
| WO | WO 2011/057299 A2 | 5/2011 |
| WO | WO 2011/057299 A3 | 7/2011 |

OTHER PUBLICATIONS

U.S. Appl. No. 13/224,666, filed Sep. 2, 2011, Belson et al.
U.S. Appl. No. 13/273,000, filed Oct. 13, 2011, Belson.
International search report and written opinion dated Oct. 13, 2010 for PCT/US2010/027321.
International search reoprt and written opinion dated Oct. 24, 2011 for PCT Application No. US2011/042036.
Office action dated Jan. 2, 2014 for U.S. Appl. No. 13/273,000.
U.S. Appl. No. 14/541,495, filed Nov. 14, 2014, Belson et al.
International search report and written opinion dated Aug. 19, 2013 for PCT Application No. US2013/040990.
Notice of allowance dated Mar. 10, 2015 for U.S. Appl. No. 13/224,666.
Office action dated Jul. 16, 2014 for U.S. Appl. No. 13/273,000.
Office action dated Oct. 2, 2014 for U.S. Appl. No. 13/224,666.
Co-pending U.S. Appl. No. 14/732,719, filed Jun. 6, 2015.
Co-pending U.S. Appl. No. 14/801,853, filed Jul. 17, 2015.
Notice of allowance dated Apr. 27, 2015 for U.S. Appl. No. 13/224,666.
Office action dated Apr. 30, 2015 for U.S. Appl. No. 14/541,495.
International search report and written opinion dated Nov. 4, 2015 for PCT Application No. US2015/043312.

* cited by examiner

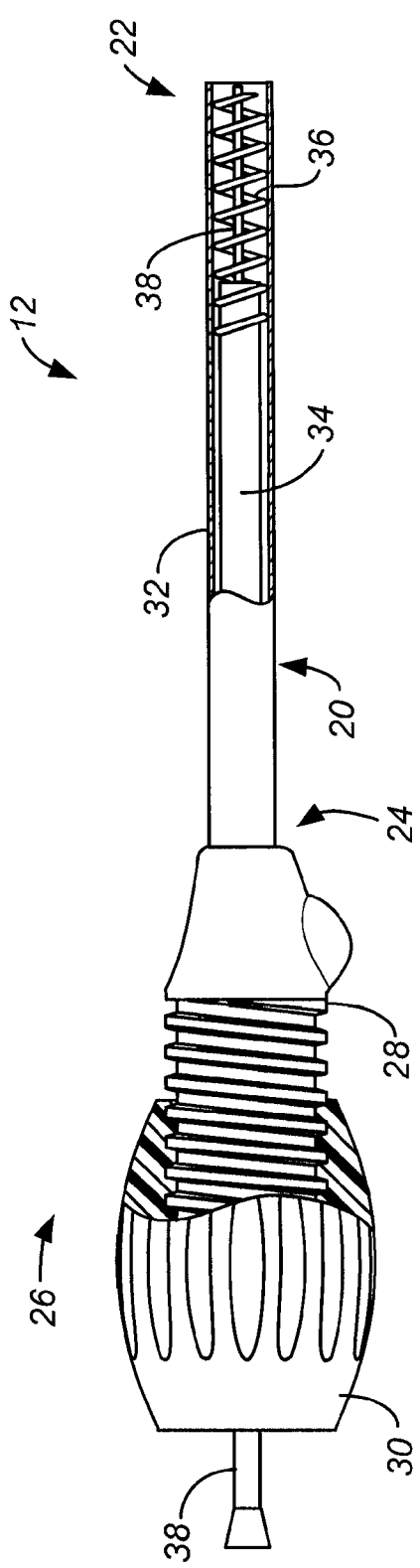
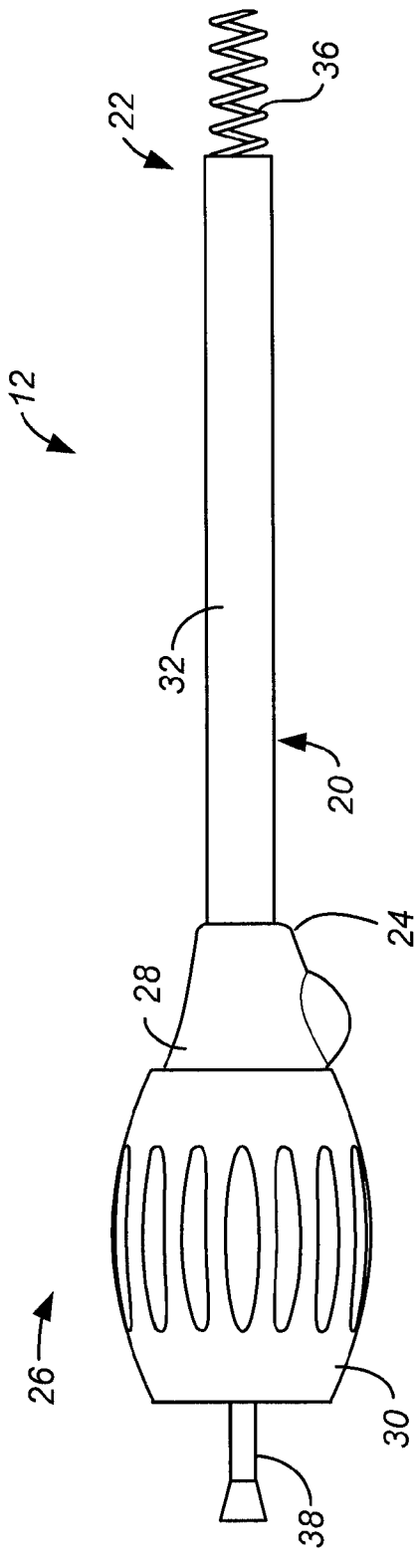
FIG. 2A
FIG. 2B

METHOD AND APPARATUS FOR TRANSAPICAL ACCESS AND CLOSURE

CROSS-REFERENCE TO RELATED APPLICATIONS

This application claims the benefit of prior provisional application No. 61/398,485, filed on Jun. 26, 2010, and of prior provisional application No. 61/402,042, filed on Aug. 23, 2010, the full disclosures of which are incorporated herein by reference.

BACKGROUND OF THE INVENTION

1. Field of the Invention

The present invention relates generally to medical apparatus and methods. More particularly, the present invention relates to methods and apparatus for providing transapical access to a heart chamber to facilitate performing various procedures within the heart chamber, such as heart valve replacement, valve repair, atrial septum repair, aneurysmectomy, and the like.

Heart valve replacement and repair on beating hearts are typically performed via a transvascular or a transapical approach. Of particular interest to the present invention, transapical access is typically established via an intercostal incision and placement of a relatively large cannula to provide access to the apex of the heart. Conventional surgical tools are then used through the cannula to form an incision into the heart to allow passage of the interventional tools used for the heart valve replacement, repair, or other procedure. Frequently, a purse string suture is pre-placed at the site of the incision to facilitate closure after the procedure is complete.

The need to use conventional surgical tools for making the incision through the apical region into the heart chamber requires that a relatively large access port be placed through the intercostal space, typically between the fourth and fifth ribs. The incision is typically 4 or 5 cm in length, and such incisions in the abdomen are very painful to the patient.

For these reasons, it would be desirable to provide improved apparatus and methods for both accessing a heart for transapical penetration and for closing the penetration after the related procedure has been completed. Such apparatus and methods would preferably require a smaller intercostal incision than has often been necessary in the past, and in particular, it would be desirable if the incision were below 5 cm, preferably below 4 cm, and still more preferably below 3 cm, or less. Methods and apparatus should further provide for both simplified access and closure protocols, should present minimum risk to the patient, be economical, and be relatively uncomplicated for use by the physician. At least some of these objectives will be met by the inventions described below.

2. Description of the Background Art

U.S. Patent Publ. Nos. 2011/0015728; 2011/0004235; and 2009/0287183 describe devices for transapically accessing a heart chamber for performing valve replacement and other procedures. U.S. Patent Publ. No 2010/0268253 describes a self-closing structure that can be disposed about a transapical access site. U.S. Pat. No. 4,204,541, describes a helical needle for performing vertical suturing in tissues including cardiac and live tissue. U.S. Pat. Nos. 7,758,595; 7,637,918; 5,545, 148; and 5,356,424; and U.S. Patent Publ. Nos. 2009/275960; 2008/275473; 2006/253127; and 2006/212048 describe other suturing devices with helical needles.

SUMMARY OF THE INVENTION

In a first aspect of the present invention, a method for transapical access to a heart chamber comprises advancing a helical needle through the myocardium to position a suture through an apical region of the heart, withdrawing the helical needle leaving the suture in place in the myocardium in a helical pattern, and thereafter dilating a passage through the helical suture into the heart chamber. The pre-placed suture is then available for closing subsequent incisions into the heart by simply drawing proximately on the suture to close such incisions. The suture is typically self-anchoring, e.g. having anchoring barbs or a T-bar at or near its distal end, and placement can be accomplished using relatively small tools, typically through an intercostal incision below 3 cm, often below 2 cm, and in some cases below 1 cm. Methods are also suitable for performing on a beating heart, although they could be used in stopped heart procedures as well. In exemplary embodiments, tension is maintained on the pericardium to stabilize the heart while the helical needle is being advanced and/or a dilator is being advanced through the helical suture (described in more detail below).

In an exemplary embodiment of the method of the present invention, the helical needle is first passed through the pericardium surrounding the heart, and the helical needle is then drawn proximately to tension the pericardium and stabilize the heart. The helical needle is then advanced into the myocardium while the tension is maintained on the pericardium. In addition or as an alternative to using the helical needle for applying traction on the pericardium, a shaft or other component of the access tool could also be provided with barbs, expanding elements, or the components suitable for engaging the pericardium and applying traction while the needle is being advanced.

In most procedures, prior to introducing the helical needle, a straight needle will be advanced through the apical region of the heart to establish an initial tissue tract through the myocardium and to confirm the correct entry point and orientation. Optionally, the needle may be used to place a guide wire, but usually the needle itself will be used as a guide for the introduction of the helical needle deployment device, as described in more detail below. In such cases, the needle may have to have a proximal hub that can be removed prior to advancement of the helical needle assembly thereover. Alternatively, the needle shaft could be long enough to allow the helical needle assembly to be pre-loaded on the straight needle prior to accessing the heart chamber.

In many cases, the present invention will use a single helical needle in order to place a single helical suture. In other embodiments, however, it may be desirable to deploy multiple helical needles, usually simultaneously using the same needle deployment shaft. In some instances, two or more helical needles may be coaxially nested with one helical needle having a smaller diameter and being disposed radially inwardly of an outer helical needle. In other instances, the two or more helical needles may be located in a common cylindrical envelope. In such cases, the needles may have penetrating tips which are rotationally offset and/or axially offset from each other.

The suture will usually be placed within the myocardium and will not extend into the heart chamber (beyond the myocardium). In such cases, use of a suture having self-deploying barbs at its distal end will be particularly useful. The barbs project partially outside of the needle as the needle is rotationally advanced into the tissue. As soon as the rotational advancement of the helical needle is stopped and reversed, however, the barbs will anchor in the tissue and hold the distal end of the suture in place as a helical needle is counter-rotated and removed from the tissue. In other instances, however, it may be desirable to advance the suture all the way into the heart chamber. In such cases, some other self-deploying anchor, such as a T-bar will find use.

Methods for establishing transapical access in accordance with the present invention will find use with a variety of intracardiac procedures that may be performed on beating hearts. In such procedures, one or more tools are introduced through the dilated passage which has been formed through the myocardium while the helical suture remains in place surrounding the tool as the tool is advanced. A cardiac procedure will be performed with the tool, and the tool(s) then removed from the dilated passage after the procedure has been completed. After the tools and any devices used for access have been removed, the dilated passage may be closed by drawing on the suture in a proximal direction, closing the helical suture loops which were pre-placed as described above. The methods herein are suitable for a wide variety of intracardiac procedures including valve replacement, valve repair, left atrial appendage closure, cardiac oblation, closure of an atrial septal defect, closure of a patent foramen ovale, and the like.

In a second aspect of the present invention, a system for establishing transapical access through myocardial tissue is provided. The system comprises a helical needle driver having a cylindrical shaft having a distal end, a proximal end, and a central passage extending between said ends. A helical needle is coupled to the distal end of the shaft, and suture is releasably carried by the helical needle. The system further comprises a dilator having a width greater than that of the cylindrical shaft, where the dilator is adapted to exchanged for the helical needle driver to enlarge a passage through the helical suture which is left in place in the myocardium. Usually, the dilator will be advanced over the straight needle or optionally over a guidewire deployed by the straight needle. The system may optionally further include a sheath or a trocar for establishing access to the pericardium from an intercostal access site or optionally from a subxiphoid access site.

In a simpler embodiment, the helical needle driver may include just the helical needle (or multiple needles as described below in connection with the methods of the present invention), fixedly attached to the distal end of the cylindrical shaft so that the needle is advanced through the tissue by rotating the entire cylindrical shaft. Preferably, however, the helical needle driver will further comprise a mechanism for rotating the helical needle relative to the cylindrical shaft to advance the helical needle through tissue and relative to the shaft itself. An exemplary driver mechanism will comprise a coaxial inner cylinder or tube which carries the helical needle(s) at its distal end. The needles may then be advanced relative to the outer cylindrical shaft by rotating and advancing the intertubular shaft relative to the outer shaft, for example using a threaded drive assembly in the handle of the shaft assembly.

In most instances, the helical needle is hollow and the suture is received into the hollow passage of the needle at least over a portion of the needle length. In other instances, however, it may be possible to serve or wrap the suture over the exterior of the needle and/or within recesses formed in the needle surface (where the needle need not be hollow). For example, the suture may be wrapped around the exterior surface of the needle so that the suture is left in a loose pattern within the myocardium, with excess suture length available for expansion or elongation when the suture is radially expanded by the dilator.

The system may optionally include other components, such as the straight needle used for initially accessing the heart chamber through the myocardium, a guidewire to optionally be placed using this straight needle, and the like. In another case, the cylindrical shaft of the needle deployment tool will be advanced over the needle and/or over the guidewire in order to establish the initial penetration through the myocardium. Another option is the use of a catheter or other guiding apparatus having a balloon or other anchor at its distal end where, after the insertion of its distal tip to the ventricle, the anchor will be deployed and the guiding apparatus retracted to provide a counter force for the dilator insertion.

BRIEF DESCRIPTION OF THE DRAWINGS

FIGS. 2A and 2B illustrate the helical needle driver of FIG. 1 in detail, with the helical needle retracted in FIG. 2A and the helical needle advanced in FIG. 2B.

DETAILED DESCRIPTION OF THE INVENTION

Figure 1:
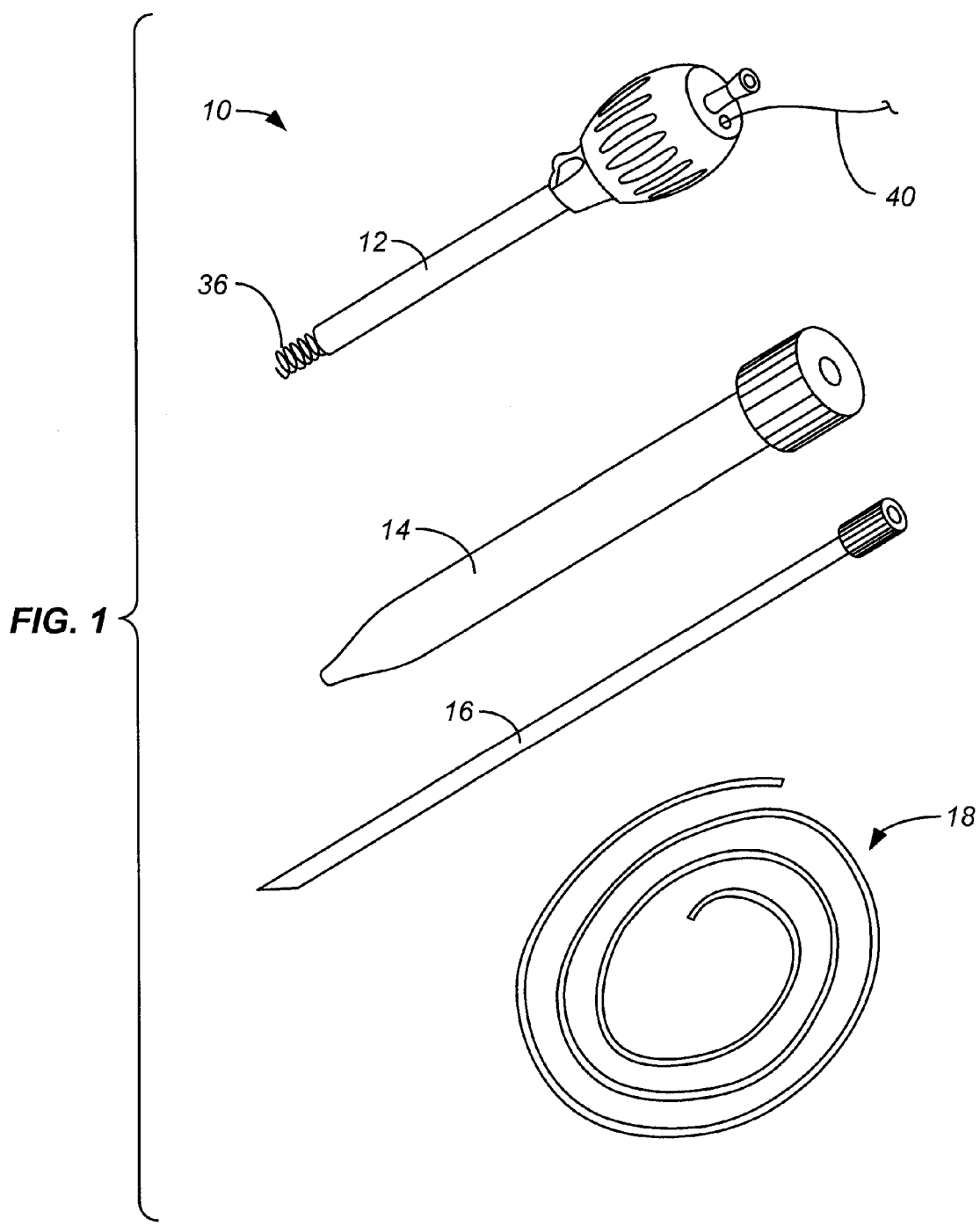
FIG. 1 illustrates a system for establishing transapical access to a heart chamber constructed in accordance with the principles of the present invention and including a helical needle driver, a dilator, a straight needle, and optionally a guidewire.

Referring to FIG. 1, a system 10 constructed in accordance with the principles of the present invention includes a helical needle driver 12, a dilator 14, a straight needle 16, and optionally a guidewire 18. The components of the system will typically be packaged together in conventional packaging, such as plastic trays, sterilized bags, boxes, and the like. The relative dimensions of each of the components will be selected to be compatible with each other. For example, both the helical needle driver 12 and dilator 14 will be sized to be advanced over either the needle 16 (in embodiments where the needle will be used as the guide for introducing these tools through the myocardium), or over the guidewire 18 (in embodiments where the driver 12 and dilator 14 will be advanced over the guidewire).

Referring now to FIGS. 2A and 2B, the helical needle driver 12 comprises a shaft assembly 20 having a distal end 22 and a proximal end 24. A drive handle 26 is attached to the proximal end 24 of the shaft assembly 20 and includes an inner threaded body 28 (FIG. 2A) and an outer rotatable member 30. The outer rotatable member 30 can be rotated over the inner threaded body 28 so that a helical needle 36 can be selectively retracted and advanced as shown in FIGS. 2A and 2B, respectively.

The inner threaded body 28 of the drive handle 26 is fixedly attached to an outer cylindrical tube 32 of the shaft assembly 20 while the outer rotatable member 30 is attached to an inner tubular member 34 (FIG. 2A). In this way, rotation of the outer rotatable member 30 over the inner threaded body 28 both rotates and advances (or retracts) the helical needle 36 which is fixedly attached to a distal end of the inner tubular member 34. Although shown as a simple helical needle, the needle in the helical needle driver can have any of the configurations shown in FIGS. 3A/B through 6A/B described below.

The helical needle driver 12 also includes a central tube 38 which extends the entire length thereof and which provides a central passage way or lumen for advancement of the driver over the straight needle 16 and/or guidewire 18, as described in more detail below.

Figure 3A:
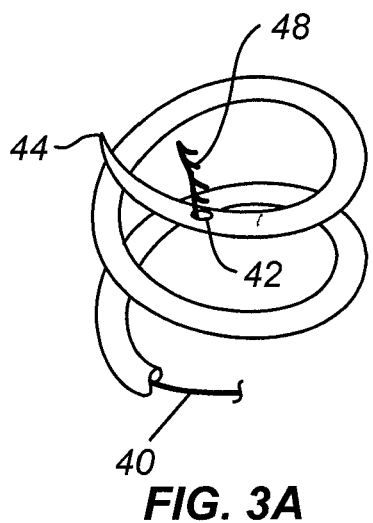
FIGS. 3A and 3B illustrate a barbed suture anchor and a T-bar suture anchor, respectively, emerging from distal end of a helical needle.
Figure 3B:
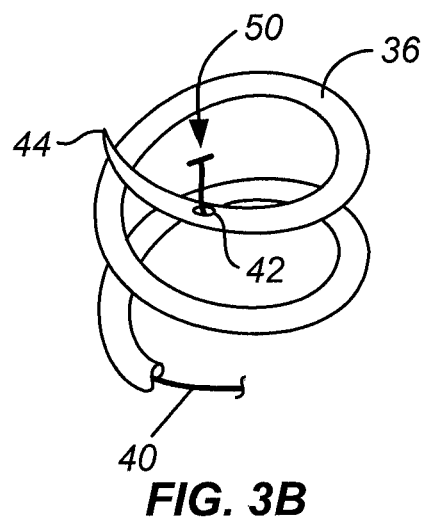

Referring to FIGS. 3A and 3B, suture 40 will typically be stowed or held within a hollow passageway through at least a distal portion of the needle 36. The suture will extend out of a small hole or port 42 disposed near the sharpened tip 44 of the needle. The suture will have an anchor formed at or over its exposed end. The anchor may be a barbed structure 48, as show in FIG. 3A, a T-Bar structure 50, as shown in FIG. 3B, or any one of a variety of other structures which allow the suture to be advanced into the tissue and which anchor within the tissue when the needle is counter-rotated and withdrawn from the tissue. The suture may be configured and/or deployed to accommodate expansion as the dilator is advanced through the helical "cage" formed after the suture is deployed. For example, the suture could be "stretchable" along its length so that the diameter of the helical cage can increase as the dilator is advanced. Alternatively, excess suture length can be stowed in and/or over the helical needle so that extra lengthing capacity is provided when the suture is left in the tissue.

Figure 4A:
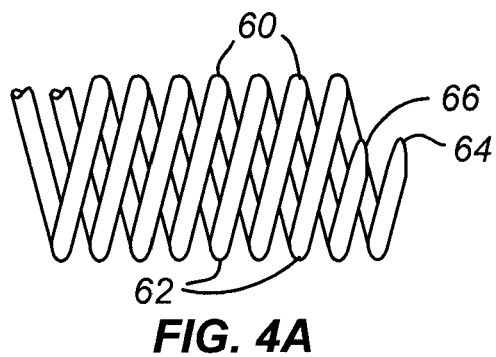
FIGS. 4A and 4B illustrate a dual needle embodiment having the sharpened needle tips axially offset.
Figure 4B:
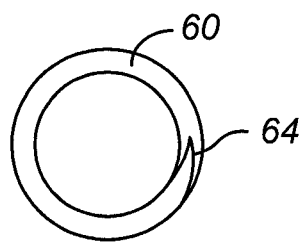
Figure 5A:
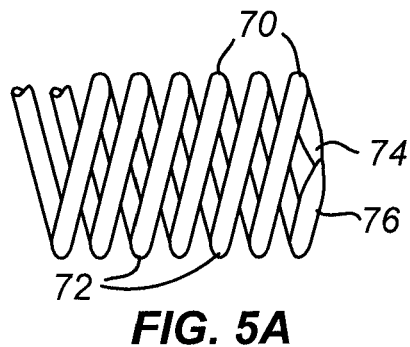
FIGS. 5A and 5B illustrate a dual needle embodiment having the sharpened needle tips being 180° offset.
Figure 5B:
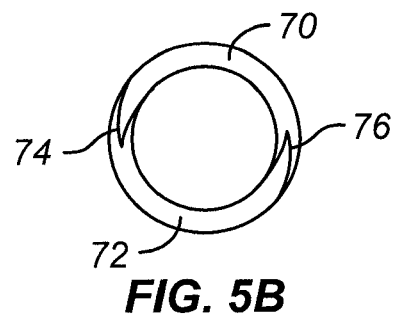
Figure 6A:
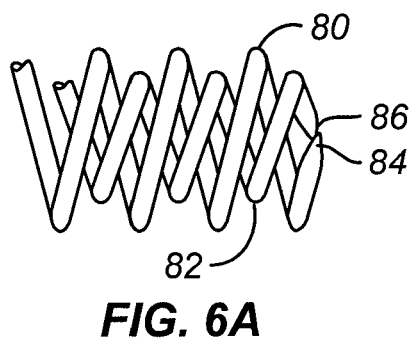
FIGS. 6A and 6B illustrate a dual needle embodiment having a larger diameter outer helical needle and a smaller diameter inner helical needle.
Figure 6B:
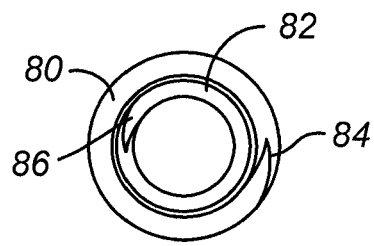

Referring now to FIGS. 4A/B through 6A/B, a variety of dual needle configurations will be described. An advantage of utilizing two, three, or even more helical needles is that a greater density of suture can be left in place in order to provide for tighter closure and constriction of the dilated passage formed through the myocardium. In FIGS. 4A/B, a pair of helical needles 16, 62 are nested so that they lie within the same cylindrical envelope while having distal tips 64 and 66, respectively, which terminate in an axially spaced-part pattern. Needles 70, 72, as shown in FIGS. 5A and 5B, are also nested so that they lie in the same cylindrical envelope, but the sharpened distal tips 74, 76, respectively, terminate at locations 180° opposed to each other. As a third alternative, helical needles 80, 82, as illustrated in FIGS. 6A/B, may be arranged in a cylindrically nested configuration where an outer helical needle 80 has a larger diameter than an inner helical needle 82. The sharpened distal tips may terminate 180° in opposition as illustrated, or could terminate in axially spaced-apart configurations (not illustrated).

Figure 7A:
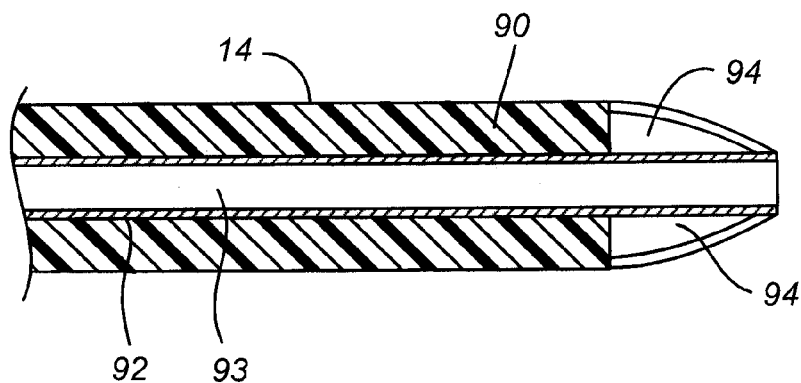
FIGS. 7A-7E illustrate exemplary dilator contractions in accordance with the principles of the present invention.
Figure 7B:
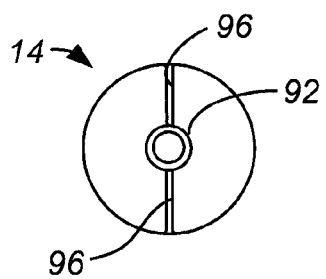
Figure 7C:
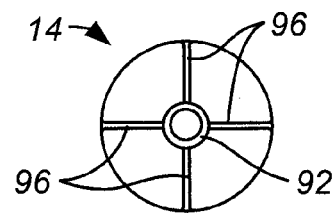
Figure 7D:
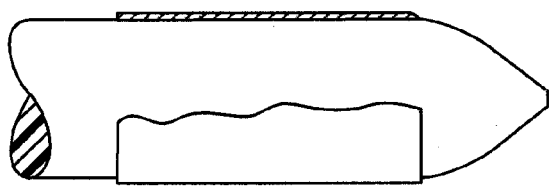
Figure 7E:
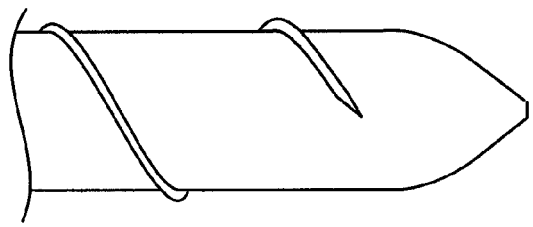

Referring now to FIGS. 7A through 7C, a dilator 14 preferably comprises a body formed from an elastomeric or other compressible material over at least its distal portion. For example, the elastomeric material may be formed into an outer tubular component 90 formed over an inner rigid tubular support 92, shown in FIG. 7A. The tube has an inner lumen 93 suitable for receiving and advancement over the access needle and/or a guidewire present in the initial tissue tract being dilated. Cutting blades 94 may be attached to a distal end of the inner support tube 92, and such blades may be recessed within protective grooves 96 as shown in FIG. 7B (as shown for a two-bladed configuration) and FIG. 7C (as shown for a four-bladed configuration). In this way, the cutting edges of the blades 94 will be protected from inadvertently cutting tissue but will be exposed when the dilator tip is engaged against particularly strong tissue or membranes which resist expansion and will require cutting, such as the pericardium. Optionally, the obturator may comprise an outer sleeve 93 and removable obturator 95 (FIG. 7D) or may have external threading 97 (FIG. 7E) to assist in advancement through the myocardium.

The blades 94 need to have widths which span the entire diameter of the dilator 14. For example, a typical dilator diameter will be 1 cm, and the blades will typically span only 2 mm to 6 mm. Alternatively or additionally, the dilator may have external threads which allow the dilator to be rotated about its axis to enhance advancement through the tissue tract.

Figure 8A:
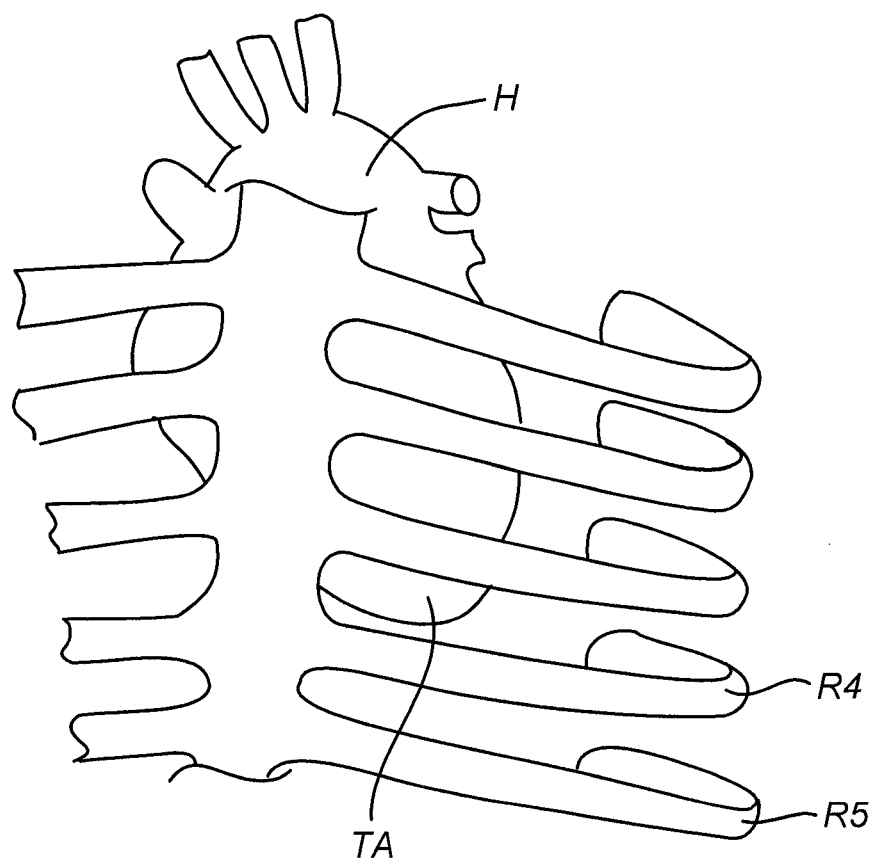
FIGS. 8A-8J illustrate an exemplary transapical access procedure and intervention performed in accordance with the principles of the present invention.

Referring now to FIGS. 8A through 8J, an exemplary protocol for transapically accessing a heart chamber and performing an intra cardiac procedure according to the principles of the present invention will be described. The relevant patient anatomy is illustrated in FIG. 8A where a transapical region TA of a patient's heart H is protected behind the patient's ribs. Access will generally be performed through the intercostal space between rib R4 and rib R5.

Figure 8B:
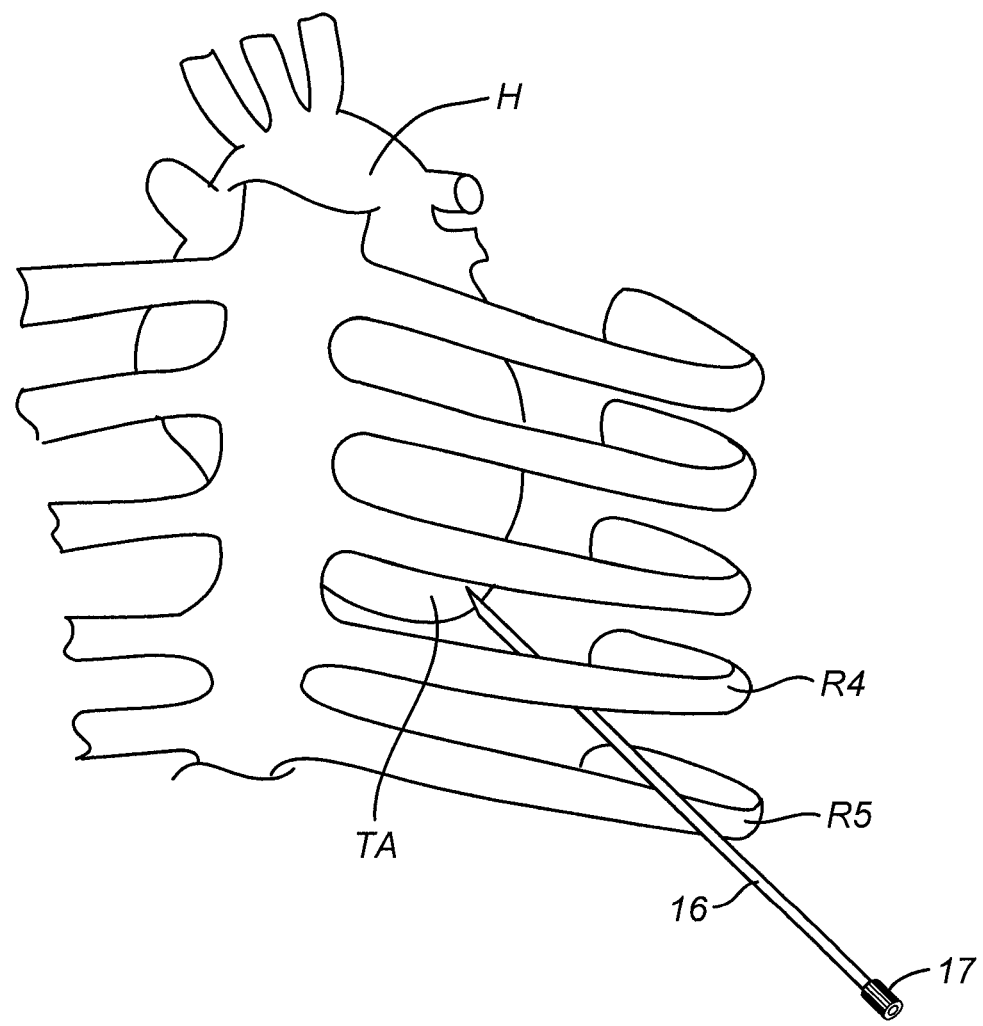

Initially, the straight needle 16 will be penetrated intercostally between ribs R4 and R5 so that the sharpened tip of the needle can enter the heart at the transapical region TA, as shown in FIG. 8B. Usually, the straight needle will be passed through a small intercostal incision, e.g., less than 3 cm, usually less than 2 cm, and often about 1 cm. To assist in guiding, the straight needle may incorporate ultrasonic or optical imaging. Alternatively, a thoracoscope or other endoscope could be deployed through a separate incision to allow visualization.

Figure 8C:
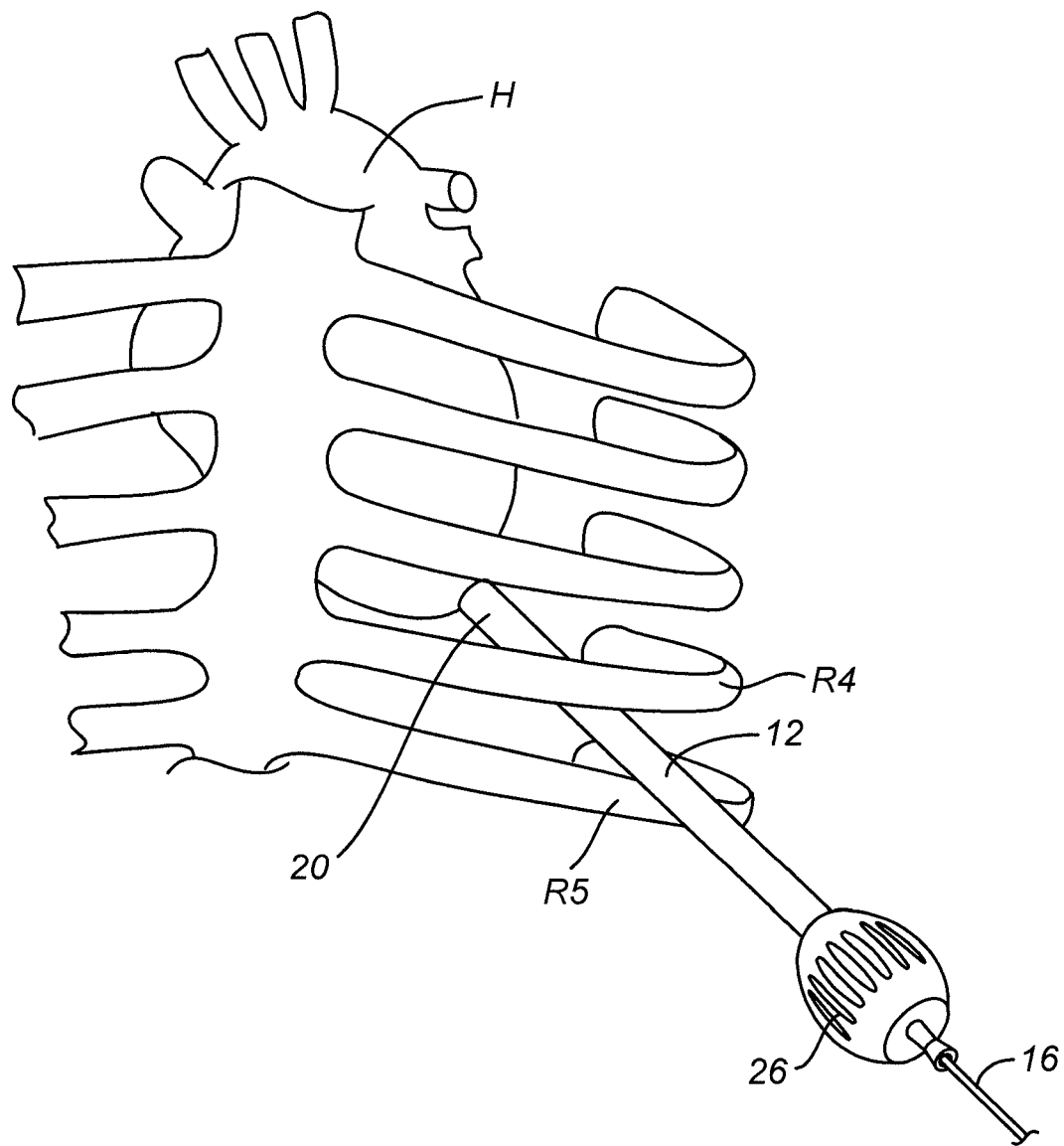

After advancing the needle through the myocardium into the left ventricle of the heart, the needle hub 17 will be removed and the helical needle driver 12 will be advanced over the needle 16, as shown in FIG. 8C. The shaft assembly 20 of the needle driver 12 will be advanced until the distal tip of the shaft engages the pericardium surrounding the myocardium of the heart.

Figure 8D:
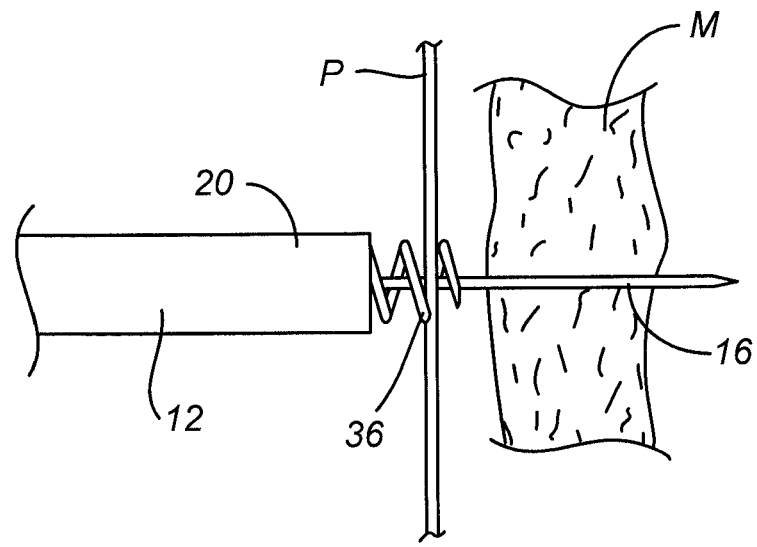

Referring now to FIG. 8D, the helical needle 36 will be advanced from the distal end of the shaft assembly 20 to initially penetrate the pericardium P. Once the needle has penetrated the pericardium, the helical needle driver 12 will be proximally retracted to apply tension to the pericardium which will help stabilize the heart and facilitate needle entry into the heart.

Figure 8E:
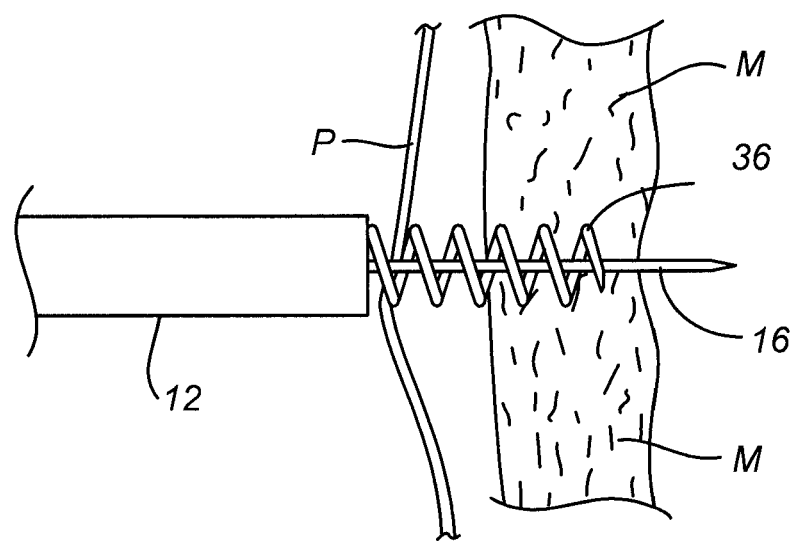

As illustrated in FIG. 8E, the helical needle 36 may be rotated and advanced into the myocardium M while the pericardium P remains under traction. Straight needle 16 also remains in place to help guide the helical needle 36.

Figure 8F:
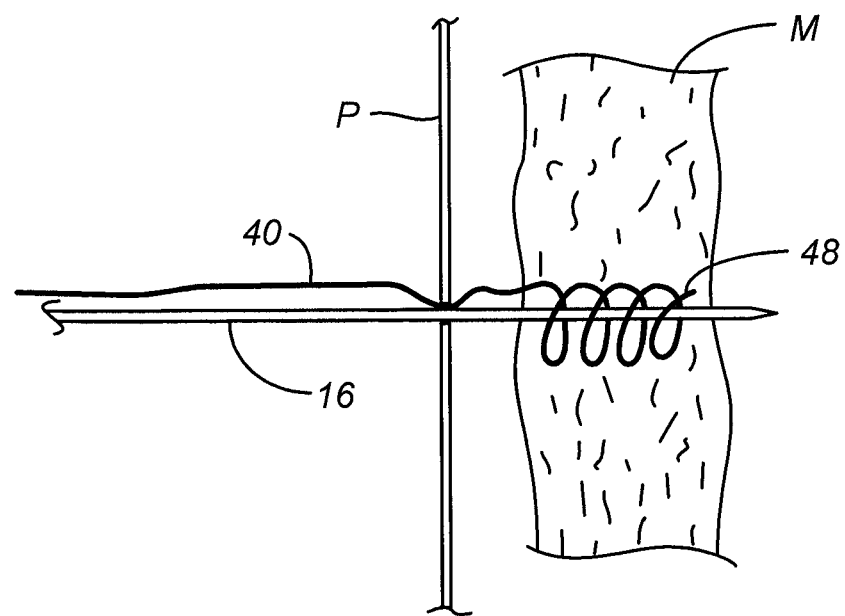

Preferably, the needle 36 will not be advanced fully into the left ventricle and, instead, needle rotation will stop and be reversed in order to leave the helical suture in place with the barb anchor 48 within the myocardium as show in FIG. 8F. At this point, the helical needle driver will be completely withdrawn, leaving the straight access (guiding) needle 60 and helical suture 40 in place.

Figure 8G:
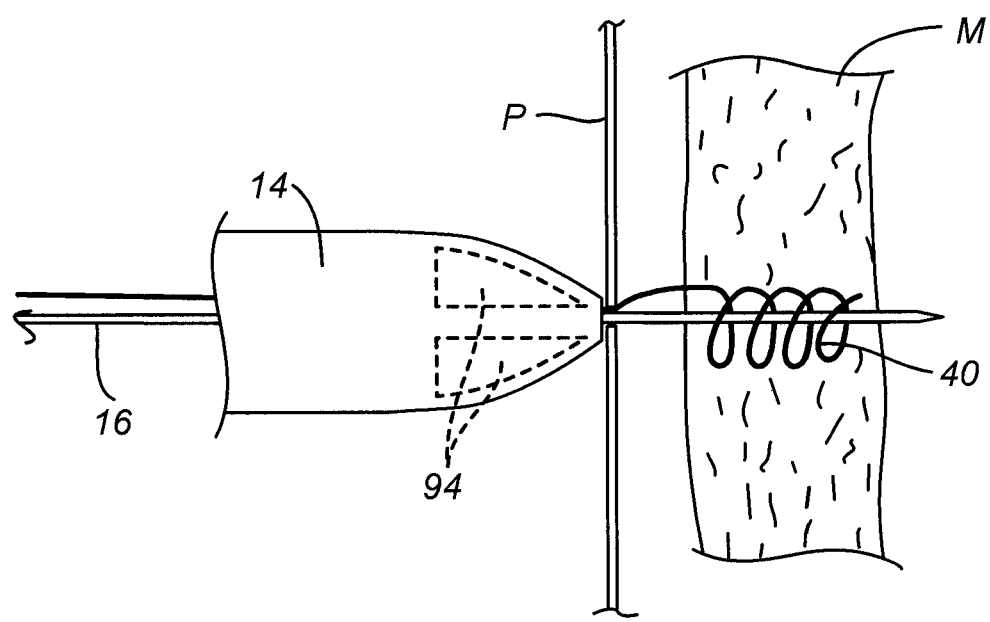
Figure 8H:
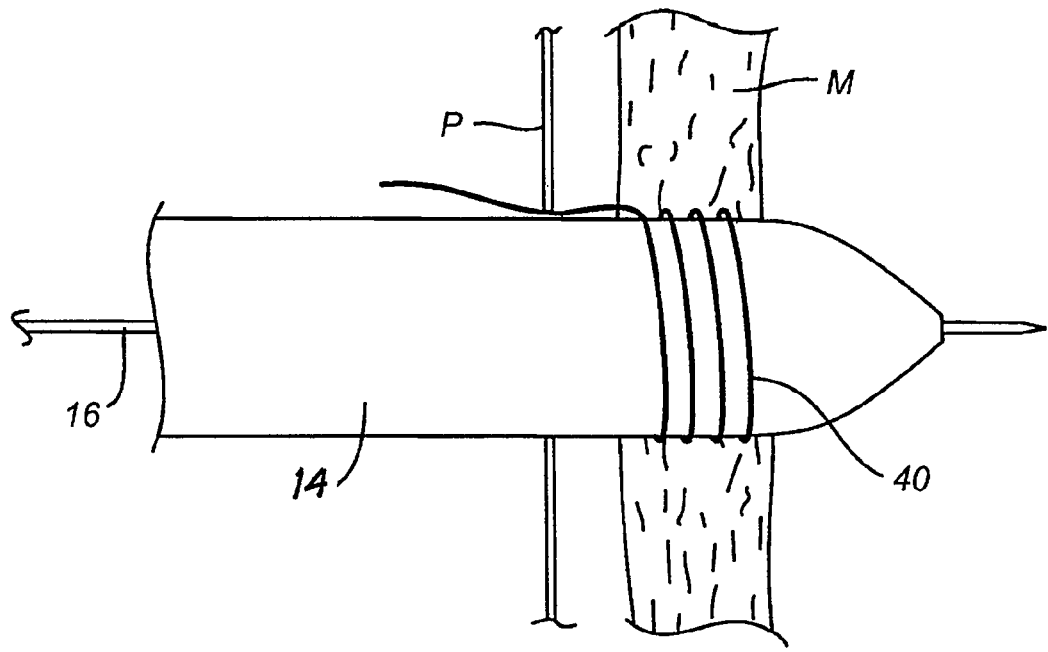

Next, as shown in FIG. 8G, the dilator 14 will be advanced over the needle 16 until its distal tip reaches the pericardium P. As the dilator 14 is advanced through the pericardium, the recessed blades 94 will be exposed as the elastomeric material surrounding them is compressed by the pericardium. The blades 94 help the dilator 14 pass through the pericardium, and the dilator is then able to enter the myocardium M as shown in FIG. 8H. As the myocardium M is not as fibrous and difficult to penetrate as the pericardium is, the elastomeric material will recover from compression and the blades 94 will again be recessed within the tip of the dilator 14 as the tip advances into the left ventricle of the heart. The blades 94 are optional, particularly if the pericardium is pre-cut prior to advancing the dilator therethrough. Blades are usually not needed to advance the dilator through the myocardium.

As the dilator 14 passes through the helical suture 40, the suture is radially expanded. Typically, extra lengths of suture will be left in place by the helical needle in order to facilitate radial expansion. For example, the suture 40 may be stowed within a central passage of the needle in a serpentine or compacted configuration where tension on the suture will extend its length. Further optionally, the needle, guidewire, or other guiding apparatus (not illustrated) may be provided with a balloon or other deployable anchor to allow a counter traction on the myocardium as the dilator is advanced.

Figure 8I:
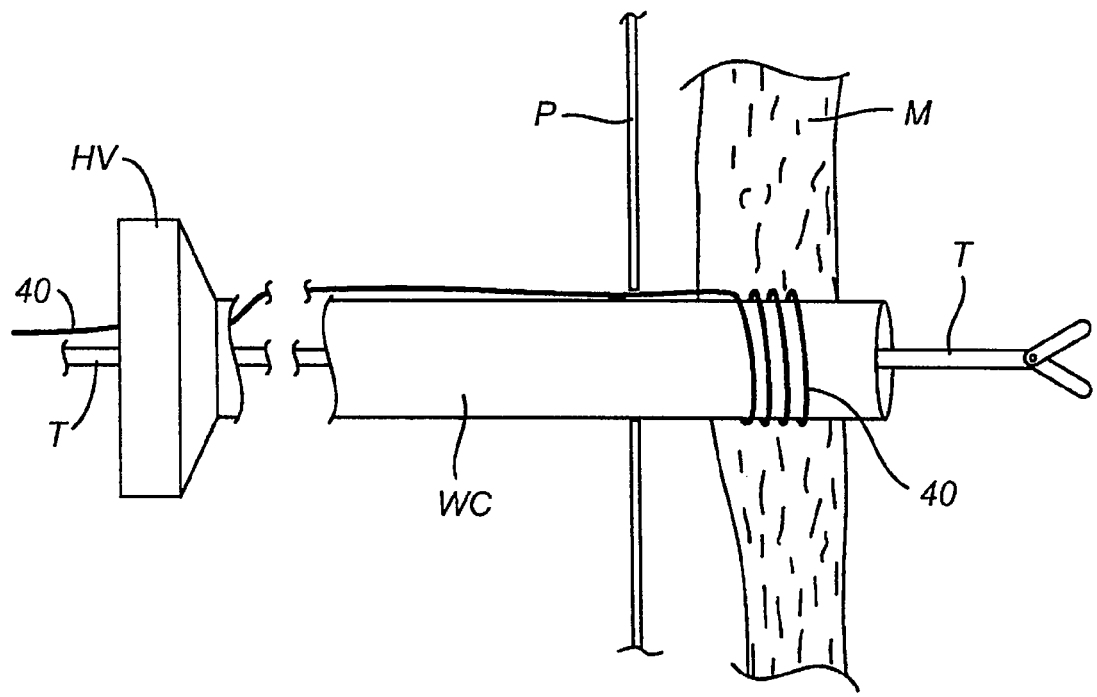

After the dilator 14 has been passed through the myocardium M, as shown in FIG. 8H, the dilator will be removed and a working cannula WC having a hemostatic value HV is placed over the needle 16 and the needle removed as shown in FIG. 8I. The working cannula provides access for working tools intended to perform any particular intra cardiac procedure desired. An exemplary tool T is illustrated, but it will be appreciated that specific tools will be associated with specific procedures. Optionally, the working cannula can be part of the dilator where a central member (obturator) of the dilator is removed to leave an outer sleeve in place as the cannula.

Figure 8J:
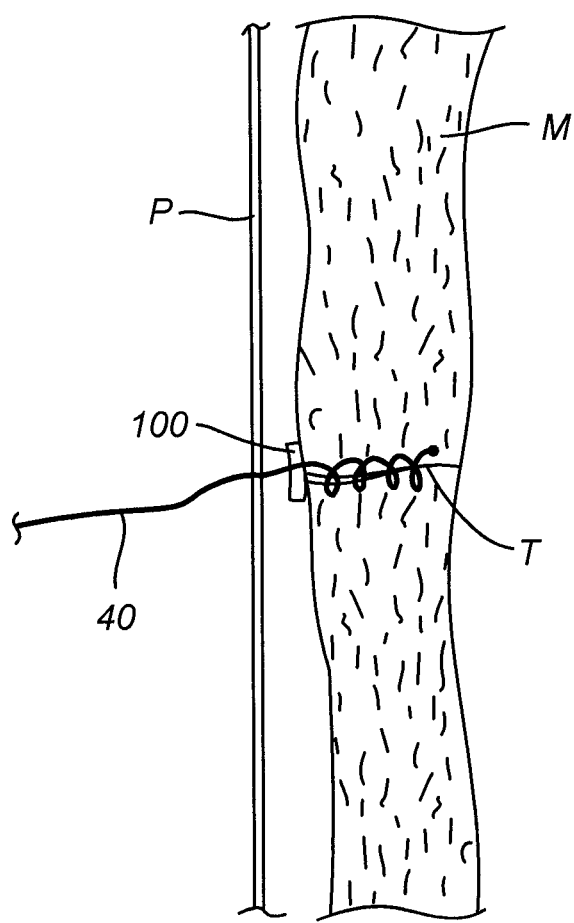

Finally, after the intra cardiac procedure is complete and the working cannula WC and all tools T removed, the suture 40 may be proximately retracted to close the helical suture loops within the myocardium to close the incision I as shown in FIG. 8J. The suture could be tied off, but more usually, a suture lock 100 will be advanced over the suture to hold the suture loops and prevent the incision I from reopening.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for transapical access to a heart chamber, said method comprising:
    positioning a guiding apparatus through a tissue tract through a myocardium of an apical region of the heart;
    advancing a helical needle over the guiding apparatus to helically position a suture surrounding the tissue tract through the apical region of the myocardium of the heart, wherein an anchor on a terminal distal end of the suture anchors in the myocardium or in the heart chamber;
    withdrawing the helical needle leaving the helical suture in place; and
    dilating the tissue tract through the helical suture into the heart chamber;
    introducing at least one tool through the dilated tissue tract while the helical suture remains in place;
    performing a cardiac procedure with the at least one tool;
    removing the at least one tool from the dilated passage; and
    drawing on the suture to close the dilated passage.

2. The method as in claim 1, wherein all method steps are performed while the heart is beating.

3. The method as in claim 1, wherein tension is maintained on a pericardium surrounding the heart to stabilize the heart while the helical needle is being advanced.

4. The method as in claim 3, wherein the helical needle is first passed through the pericardium surrounding the heart, the helical needle is then drawn proximally to tension the pericardium and stabilize the heart, and the helical needle is advanced into the myocardium while the tension is maintained on the pericardium.

5. The method as in claim 1, wherein the helical needle is first positioned adjacent the apical region of the heart via an intercostal approach.

6. The method as in claim 1, wherein the helical needle is first positioned adjacent the apical region of the heart via a subxiphoid approach.

7. The method as in claim 1, wherein positioning the guiding apparatus comprises advancing a straight needle through the apical region prior to advancing the helical needle.

8. The method as in claim 7, further comprising visualizing advancement of the straight needle.

9. The method as in claim 7, wherein a guidewire is placed through the straight needle and the helical needle is advanced over the guidewire.

10. The method as in claim 1, wherein the guiding apparatus is positioned through an intercostal penetration and through the myocardium, and wherein dilating the tissue tract comprises advancing a dilator over said guiding apparatus while a counter traction is applied to the heart with the guiding apparatus.

11. The method as in claim 1, wherein advancing comprises advancing two or more helical needles simultaneously to position two or more helical sutures.

12. The method as in claim 11, wherein the two or more helical needles are coaxially nested with a radially inner needle and a radially outer needle.

13. The method as in claim 11, wherein the two or more helical needles are located in a common cylindrical envelope.

14. The method as in claim 13, wherein the two or more helical needles have tissue penetrating tips which are rotationally offset.

15. The method as in claim 13, wherein the two or more helical needles have tissue penetrating tips which are axially offset.

16. The method as in claim 1, wherein the anchor on the distal end of the suture anchors in the myocardium.

17. The method as in claim 16, wherein the anchor comprises self-deploying barbs which anchor when the suture is tensioned proximally.

18. The method as in claim 1, wherein the anchor on the distal end of the suture anchors in the heart chamber.

19. The method as in claim 1, wherein the anchor comprises T-bar anchor.

20. The method as in claim 1, wherein the cardiac procedure comprises valve replacement.

21. The method as in claim 1, wherein the cardiac procedure comprises valve repair.

22. The method as in claim 1, wherein the cardiac procedure comprises left atrial appendage closure.

23. The method as in claim 1, wherein the cardiac procedure comprises cardiac ablation.

24. The method as in claim 1, wherein the cardiac procedure comprises closure of an atrial septal defect.

25. The method as in claim 1, wherein the cardiac procedure comprises closure of a patent foramen ovale.

26. The method as in claim 1, wherein the cardiac procedure comprises an aneurysmectomy.

* * * * *